US008582106B2

(12) United States Patent
Palumbo et al.

(10) Patent No.: US 8,582,106 B2
(45) Date of Patent: Nov. 12, 2013

(54) AUTOMATIC OPTICAL MEASUREMENT SYSTEM AND METHOD

(75) Inventors: Perry A. Palumbo, Fort Collins, CO (US); Brian Harmon, Loveland, CO (US)

(73) Assignee: Hach Company, Loveland, CO (US)

( * ) Notice: Subject to any disclaimer, the term of this patent is extended or adjusted under 35 U.S.C. 154(b) by 599 days.

(21) Appl. No.: 12/739,988

(22) PCT Filed: Nov. 4, 2008

(86) PCT No.: PCT/US2008/082349
§ 371 (c)(1),
(2), (4) Date: Apr. 27, 2010

(87) PCT Pub. No.: WO2009/061729
PCT Pub. Date: May 14, 2009

(65) Prior Publication Data
US 2010/0245827 A1    Sep. 30, 2010

Related U.S. Application Data

(60) Provisional application No. 60/986,740, filed on Nov. 9, 2007.

(51) Int. Cl.
*G01N 21/00* (2006.01)

(52) U.S. Cl.
USPC .......... 356/440; 250/573; 250/364; 250/435; 356/441; 356/442

(58) Field of Classification Search
USPC .......... 250/573, 574, 364, 435; 356/441–442
See application file for complete search history.

(56) References Cited

U.S. PATENT DOCUMENTS

| | | |
|---|---|---|
| 3,636,635 A | 1/1972 | Lemelson |
| 3,923,403 A | 12/1975 | Harklau |
| 3,964,867 A | 6/1976 | Berry |
| 3,995,168 A | 11/1976 | Neuscheler et al. |
| 4,077,724 A | 3/1978 | Briggs |
| 4,229,107 A | 10/1980 | Childers |
| 4,279,078 A | 7/1981 | Hinshaw et al. |
| 4,290,997 A | 9/1981 | Suovaniemi |
| 4,311,047 A | 1/1982 | Hubbard, Jr. et al. |
| 4,313,340 A | 2/1982 | Schniewind |
| 4,333,016 A | 6/1982 | Bilstad et al. |
| 4,338,546 A | 7/1982 | Ehret et al. |
| 4,603,977 A * | 8/1986 | Bennett et al. ............... 356/436 |
| 4,631,529 A | 12/1986 | Zeitz |
| 4,779,462 A | 10/1988 | Boullet et al. |

(Continued)

FOREIGN PATENT DOCUMENTS

| | | |
|---|---|---|
| EP | 1054250 A1 | 11/2000 |
| GB | 2193313 A | 2/1988 |
| WO | 9307472 | 4/1993 |

*Primary Examiner* — Gregory J Toatley
*Assistant Examiner* — Iyabo S Alli
(74) *Attorney, Agent, or Firm* — Ference & Associates LLC

(57) ABSTRACT

An automatic optical measurement system (100) is provided. The measurement system (100) includes a sample vial (10) and an automatic optical measurement apparatus (90) configured to receive the sample vial (10). The automatic optical measurement apparatus (90) is configured to detect a presence of the sample vial (10) in the automatic optical measurement apparatus (90) and measure a light intensity of light substantially passing through the sample vial (10) if the sample vial (10) is present. The measured light intensity is related to sample material properties of a sample material within the sample vial (10).

6 Claims, 9 Drawing Sheets

(56) References Cited

U.S. PATENT DOCUMENTS

| | | |
|---|---|---|
| 4,816,695 A | 3/1989 | Lavin |
| 4,834,497 A | 5/1989 | Angel |
| 4,926,702 A | 5/1990 | Stephens et al. |
| 5,099,454 A | 3/1992 | Dieulesaint et al. |
| 5,168,240 A | 12/1992 | Howe |
| 5,171,530 A | 12/1992 | Pennatto |
| 5,508,521 A | 4/1996 | Kraft et al. |
| 6,113,858 A | 9/2000 | Tang et al. |
| 6,452,676 B1 | 9/2002 | Kawamura |
| 6,522,345 B1 | 2/2003 | Alexander |
| 6,592,822 B1 * | 7/2003 | Chandler ........................ 356/73 |
| 6,612,188 B2 | 9/2003 | Hamilton |
| 6,831,733 B2 | 12/2004 | Pattersson et al. |
| 7,237,441 B2 | 7/2007 | Umekage et al. |
| 7,239,157 B2 | 7/2007 | Stellari et al. |
| 2005/0106746 A1 | 5/2005 | Shinn et al. |
| 2005/0250173 A1 * | 11/2005 | Davis et al. ................... 356/343 |
| 2006/0238764 A1 | 10/2006 | Hafeman et al. |

* cited by examiner

SECTION AA

SECTION AA

AUTOMATIC OPTICAL MEASUREMENT SYSTEM AND METHOD

FIELD OF THE INVENTION

The invention is related to the field of optical measurements, and more specifically, to an automatic optical measurement system and method.

BACKGROUND OF THE INVENTION

There exist many examples of devices that detect the presence or absence of a liquid in a fixed optical arrangement in which the liquid flows through or comes in contact with the apparatus. The liquid is detected by means of optical absorption or reflection, conductivity, physical displacement, ultrasonic, and or capacitive means, but none of which are suitable for use with colorimeters, spectrophotometers, or other optical measuring devices without additional cost and or complexity. More specifically a need exists for the automatic measure of the transmittance of light through a sample wherein a removable vessel contains a biologically active pathogen or toxic substance. It is often desirable to measure the concentration of such hazardous materials without manual manipulation of the controls of the measuring apparatus so as to prevent contamination or contaminate transfer from one operator to another via the apparatus controls.

A unique aspect of the present invention is that a single optical path is used for the detection and measure of the sample concentration. Prior art inventions such as that of Harklau, U.S. Pat. No. 3,923,403, and Briggs, U.S. Pat. No. 4,077,724, measure optical density but do not sense presence of the liquid nor automatically measure the optical density. Prior inventions such as Bilstad et al., U.S. Pat. No. 4,333,016, Zeitz, U.S. Pat. No. 4,631,529, Lavin, U.S. Pat. No. 4,816,695, and Kraft et al., U.S. Pat. No. 5,508,521 measure presence of a liquid but are unable to measure the density of the detected liquid due to limitations of the optical systems employed. Prior art Boullet et al., U.S. Pat. No. 4,779,462 does automatic measurement of mud in a liquid, but does so by utilization of separate detection and measurement means, as of conductivity of the liquid and displacement—not using a direct optical measure of the light absorption by the liquid.

An objective of the present invention is to provide an automatic means to initiate a measurement cycle in a optical density meter, colorimeter, or spectrophotometer upon insertion or extraction of a sample or vessel (vial, cuvette, test tube, or the like), in order to eliminate cross-contamination of the measurement device with biologically active pathogens or toxic substance that may be present on the surfaces of the sample.

An automatic measurement that is controlled according to the insertion and removal of does not requiring physical contact with the controls of the device in order to initiate a measurement cycle, thus improving measurement efficiency and reducing the number of contacts and steps required by the operator in order to perform an optical measurement.

Another objective of an automatic means is that the automatic measurement cycle be configurable as continuous, discrete, or for a sequence of measures, for the duration of the presence of the sample within the measurement apparatus.

It is also an objective of the invention to eliminate the need for a separate means for the initiation of the measurement cycle from that of the means used for the measurement.

It is also an objective of the invention that the automatic means be repetitive, requiring no additional action other than removal of the vial or cuvette from the device in order to prepare the device for the next vial insertion initiated measurement cycle.

Still another objective of the invention is prevent contamination and intrusion of the internal workings of the apparatus that cannot be easily disinfected or reached, or would otherwise adversely effect the operation of the apparatus in the event of a spillage of a content of the vial; (i.e., spillage of a biologically active pathogens or toxic substance is contained to external surfaces of the apparatus).

It is a further objective of the present invention that the automatic measurement means maintains readiness with minimal power consumption so as to be useful for long periods of time as in battery-powered applications.

ASPECTS OF THE INVENTION

In one aspect of the invention, an automatic optical measurement system comprises:
 a sample vial; and
 an automatic optical measurement apparatus configured to receive the sample vial, with the automatic optical measurement apparatus being configured to detect a presence of the sample vial in the automatic optical measurement apparatus and measure a light intensity of light substantially passing through the sample vial if the sample vial is present, wherein the measured light intensity is related to sample material properties of a sample material within the sample vial.

Preferably, the automatic optical measurement apparatus is configured to emit light into a sample vial region, measure light intensity of the light passing substantially through the sample vial region, detect a presence of the sample vial in the sample vial region using the measured light intensity, and determine one or more sample material characteristics of a sample material in the sample vial if the sample vial is present.

Preferably, the apparatus comprises a measurement chamber adapted to receive a sample vessel including a sample under test, a light source configured to emit light into the measurement chamber along an optical path, and a detector positioned substantially in the optical path, wherein the detector is configured to measure light intensity of light from the light source.

Preferably, the automatic optical measurement apparatus further comprises a processor configured to process the measured light intensity from the detector and determine a decrease in the light intensity along the optical path.

Preferably, the automatic optical measurement apparatus further comprises a controller configured to energize the light source when the sample vessel is at least partially in the measurement chamber and is further configured to de-energize the light source when the sample vessel is not at least partially in the measurement chamber.

Preferably, the automatic optical measurement apparatus further comprises a controller configured to gate the light emitted by the light source.

Preferably, the index of refraction of the sample vial is greater than the index of refraction of air.

Preferably, the sample vial is of a known sample dimension.

Preferably, a light transmittance value is determined by a change in intensity of light transmitted through a sample material of a known sample dimension.

Preferably, a light absorbance value is determined by a change in intensity of light transmitted through a sample material of a known sample dimension.

Preferably, a concentration value is determined by a change in intensity of light transmitted through a sample material of a known sample dimension.

Preferably, the automatic optical measurement apparatus is configured to detect an insertion of the sample vial.

Preferably, the automatic optical measurement apparatus is configured to detect an insertion of the sample vial wherein the insertion initiates a measurement process.

Preferably, the automatic optical measurement apparatus is configured to detect a removal of the sample vial.

In one aspect of the invention, an automatic optical measurement method comprises:
  detecting a presence of a sample vial in an automatic optical measurement apparatus; and
  measuring a light intensity of light substantially passing through the sample vial if the sample vial is present, wherein the measured light intensity is related to sample material properties of a sample material within the sample vial.

Preferably, the detecting further comprises detecting the presence of the sample vial if the measured light intensity is less than or equal to a predetermined vial threshold.

Preferably, the detecting further comprises detecting an absence of the sample vial if the measured light intensity exceeds a predetermined vial threshold.

Preferably, the detecting further comprises detecting an insertion of the sample vial if the measured light intensity is less than or equal to a predetermined vial threshold and if a previously measured light intensity exceeded the predetermined vial threshold.

Preferably, further comprising detecting a continuing presence of the sample vial if the measured light intensity is less than or equal to a predetermined vial threshold and if a previously measured light intensity was less than or equal to the predetermined vial threshold.

Preferably, further comprising detecting a removal of the sample vial if the measured light intensity exceeds the predetermined vial threshold and if a previously measured light intensity was less than or equal to the predetermined vial threshold.

Preferably, further comprising the preliminary step of determining and storing a predetermined vial threshold.

Preferably, further comprising the preliminary step of determining and storing a dark value.

Preferably, further comprising the preliminary step of obtaining a preliminary measured light intensity without the automatic optical measurement apparatus generating light and storing the preliminary measured light intensity as a dark value.

Preferably, further comprising subtracting a dark value from the measured light intensity, wherein the dark value comprises an error quantification.

Preferably, further comprising determining a light transmittance value, with the light transmittance value comprising the measured light intensity, minus a dark value, divided by a zero absorption value.

Preferably, further comprising determining a light transmittance value, with the light transmittance value comprising the measured light intensity, minus a dark value, divided by a zero absorption value, and determining a light absorbance value, with the light absorbance value comprising the (−log 10) transform of the light transmittance value.

Preferably, further comprising determining a path length value, with the path length value comprising a sample material thickness divided by a reference thickness, with the reference thickness being related to the sample material thickness at a known sample material absorption coefficient.

Preferably, further comprising determining a light transmittance value, with the light transmittance value comprising the measured light intensity, minus a dark value, divided by a zero absorption value, determining a path length value, with the path length value comprising a sample material thickness divided by a reference thickness, with the reference thickness being related to the sample material thickness for a known sample material absorption coefficient, and determining a sample material concentration value, with the sample material concentration value comprising the light absorbance value divided by the product of the path length value and a sample material absorption coefficient.

In one aspect of the invention, an automatic optical measurement method comprises:
  emitting light into a sample vial region;
  measuring light intensity of the light passing substantially through the sample vial region;
  detecting a presence of a sample vial in the sample vial region using the measured light intensity; and
  determining one or more sample material characteristics of a sample material in the sample vial if the sample vial is present.

Preferably, the detecting further comprises detecting the presence of the sample vial if the measured light intensity is less than or equal to a predetermined vial threshold.

Preferably, the detecting further comprises detecting an absence of the sample vial if the measured light intensity exceeds a predetermined vial threshold.

Preferably, the detecting further comprises detecting an insertion of the sample vial if the measured light intensity is less than or equal to a predetermined vial threshold and if a previously measured light intensity exceeded the predetermined vial threshold.

Preferably, further comprising detecting a continuing presence of the sample vial if the measured light intensity is less than or equal to a predetermined vial threshold and if a previously measured light intensity was less than or equal to the predetermined vial threshold.

Preferably, further comprising detecting a removal of the sample vial if the measured light intensity exceeds the predetermined vial threshold and if a previously measured light intensity was less than or equal to the predetermined vial threshold.

Preferably, further comprising the preliminary step of determining and storing a predetermined vial threshold.

Preferably, further comprising the preliminary step of determining and storing a dark value.

Preferably, further comprising the preliminary step of obtaining a preliminary measured light intensity without the automatic optical measurement apparatus generating light and storing the preliminary measured light intensity as a dark value.

Preferably, further comprising subtracting a dark value from the measured light intensity, wherein the dark value comprises an error quantification.

Preferably, further comprising determining a light transmittance value, with the light transmittance value comprising the measured light intensity, minus a dark value, divided by a zero absorption value.

Preferably, further comprising determining a light transmittance value, with the light transmittance value comprising the measured light intensity, minus a dark value, divided by a zero absorption value, and determining a light absorbance value, with the light absorbance value comprising the (−log 10) transform of the light transmittance value.

Preferably, further comprising determining a path length value, with the path length value comprising a sample material thickness divided by a reference thickness, with the reference thickness being related to the sample material thickness for a known sample material absorption coefficient.

Preferably, further comprising determining a light transmittance value, with the light transmittance value comprising the measured light intensity, minus a dark value, divided by a zero absorption value, determining a path length value, with the path length value comprising a sample material thickness divided by a reference thickness, with the reference thickness being related to the sample material thickness for a known sample material absorption coefficient, and determining a sample material concentration value, with the sample material concentration value comprising the light absorbance value divided by the product of the path length value and a sample material absorption coefficient.

BRIEF DESCRIPTION OF THE DRAWINGS

The same reference number represents the same element on all drawings. It should be understood that the drawings are not necessarily to scale.

DETAILED DESCRIPTION OF THE INVENTION

FIGS. 1-9 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
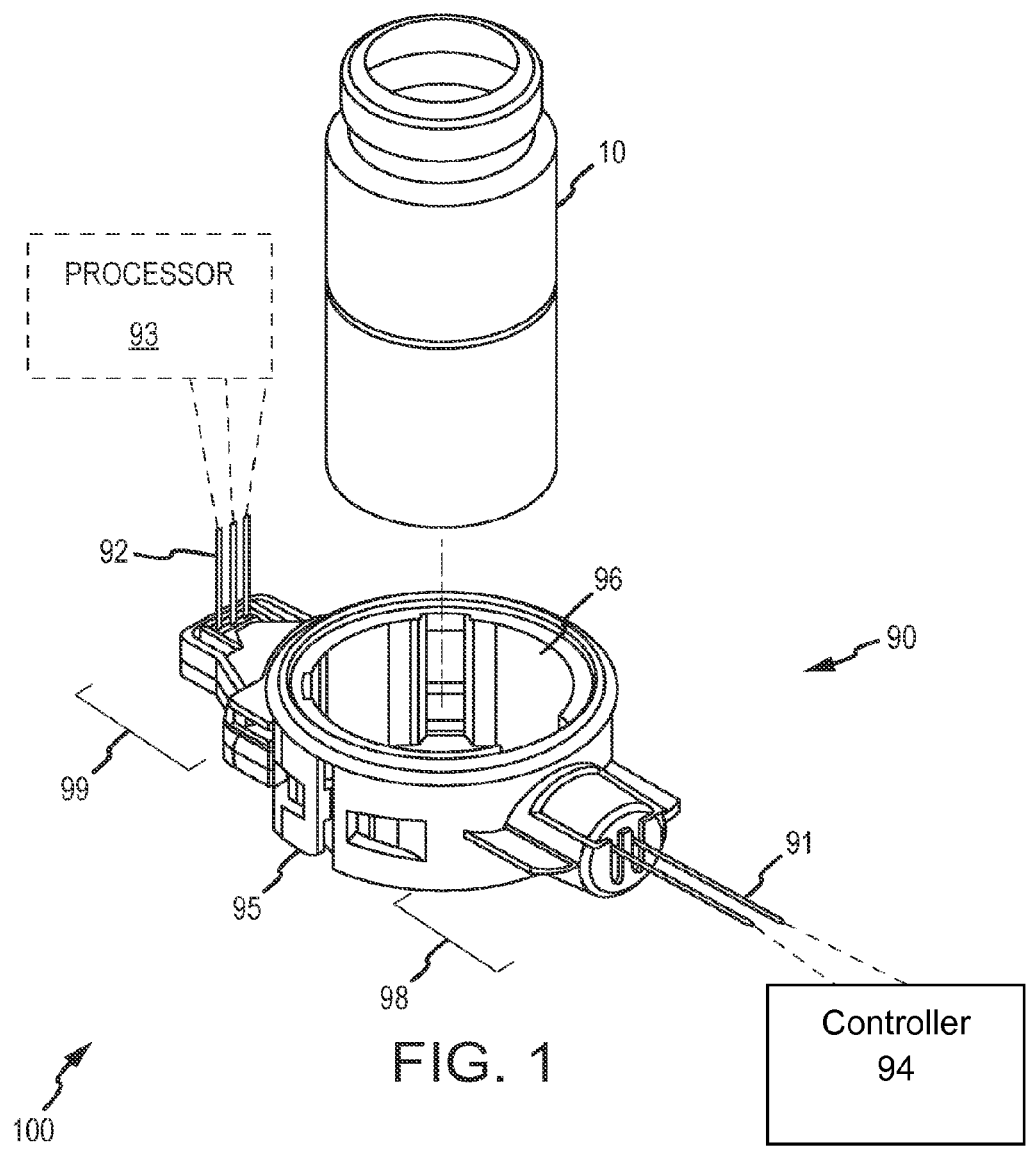
FIG. 1 shows an automatic optical measurement system according to the invention.

FIG. 1 shows an automatic optical measurement system 100 according to the invention. The automatic optical measurement system 100 includes a sample vial 10 and an automatic optical measurement apparatus 90. The sample vial 10 fits into a measurement chamber 96 of the automatic optical measurement apparatus 90. Placement of the sample vial 10 at least partially into the measurement chamber 96 in some embodiments initiates an automated optical measurement. In some embodiments, the sample vial 10 may have to be substantially fully inserted into the measurement chamber 96.

Removal of the sample vial 10 from the measurement chamber 96 likewise ends the measurement process. Consequently, the measurement process can comprise the sole actions of inserting and removing the sample vial 10 (or sequentially inserting and removing a series of vials). As a result, a user does not have to operate controls or select settings of the automatic optical measurement apparatus 90. The user does not have to touch or contact the automatic optical measurement apparatus 90. No time is wasted in the user needing to initiate and terminate the test process. Further, the user is not exposed to or in contact with the sample material. The automatic optical measurement apparatus 90 is not exposed to or in contact with the sample material. In practice, the invention eliminates the need to manually manipulate the controls of a colorimeter, spectrophotometer, or any optical device where repetitive measure of absorption are to be performed on like samples.

The automatic optical measurement apparatus 90 includes a body 95, a light source portion 98, and a light detector portion 99. The body 95 provides a structure that holds the light source portion 98 and the light detector portion 99 in a substantially co-linear relationship. The light source portion 98 includes power leads 91 that supply electrical power. The light detector portion 99 includes measurement leads 92 that transfer electrical measurement signals generated by the automatic optical measurement apparatus 90.

The light source portion 98 and the light detector portion 99 are positioned substantially co-linearly along an optical path that passes through at least a portion of the measurement chamber 96. The optical path can pass through the center of the measurement chamber 96. Alternatively, the optical path can be offset from the center of the measurement chamber 96.

The automated optical measurement comprises emitting light through the sample vial 10 and measuring a change in the received light. The change is a result of interaction with the sample material in the sample vial 10. The change in the received light may be processed in order to detect, identify, and/or analyze the sample material in the sample vial 10. Regardless of the presence or absence of the sample vial 10, or of the presence or absence of a sample material in the vial 10, at least some of the light from the light source portion 98 will be received at and measured by the light detector portion 99.

The measurement chamber 96 and the sample vial 10 have substantially the same shape so that the sample vial 10 can fit into the measurement chamber 96. The may be some clearance between the sample vial 10 and the sides of the measurement chamber 96.

The measurement chamber 96 and the sample vial 10 can have any desired shape. The cylindrical shape in the figure is just one possibility, and the two components are not limited to any particular shape, size, or proportion.

The body 95 can be formed of any suitable material. In some embodiments, the body 95 is formed of a material that is transparent to the wavelengths of light emitted from light source 6 shown in FIG. 2. This may include or be limited to wavelengths of light passed by a filter 9. Alternatively, the body 95 can be constructed of an opaque material including a first transparent window for the transmittance of light into the measurement chamber 96 and with a second transparent window for the transmittance of light out of the measurement chamber 96. Further, the body 95 (or alternatively just the measurement chamber 96) can include regions or portions of light absorbing or reflecting material, wherein the possibility of stray light reaching the detector 4 is minimized.

The sample vial 10 can likewise be formed of any suitable material. In some embodiments, the sample vial 10 is formed of a material that is transparent to the wavelengths of light emitted from light source 6 and/or passed by the filter 9. In addition, the sample vial can include one or more light transmissive regions, and does not have to be formed entirely of a light transmissive material.

The automatic optical measurement system 100 can further include a processor 93 (see FIG. 1). The processor 93 can be coupled to the detector 4 by the measurement leads 92. The processor 93 can receive light intensity measurements from the detector. The processor 93 can process the light intensity measurements in order to control the automatic optical measurement apparatus 90 and perform automatic optical measurements. The processor 93 can process the light intensity measurements in order to detect an absence or presence of the sample vial 10. The processor 93 can process the light intensity measurements in order to detect insertion and removal of the sample vial 10. The processor 93 can process the light intensity measurements in order to detect an absence or presence of a sample material in the sample vial 10. The processor 93 can process the light intensity measurements in order to determine an amount of light absorption and light transmittance. The processor 93 can process the light intensity measurements in order to determine one or more characteristics of a sample material in the sample vial 10. The processor 93 can process the light intensity measurements in order to detect, identify, and/or analyze the sample material in the sample vial 10.

The automatic optical measurement system 100 can further include a controller 94. The controller 94 can be coupled to the light source 6 by the power leads 91. The controller 94 can energize and de-energize the light source 6 as needed.

In some embodiments, the controller 94 can be coupled to the processor 93, wherein the processor 93 controls the energization of the light source 6 for performing light intensity measurements. Alternatively, the controller 94 can comprise a sub-unit or part of the processor 93.

In operation, the automatic optical measurement apparatus 90 in some embodiments is configured to detect a presence of a sample vial in an automatic optical measurement apparatus and measure a light intensity of light substantially passing through the sample vial if the sample vial is present. The measured light intensity is related to sample material properties of a sample material within the sample vial.

In operation, the automatic optical measurement apparatus 90 in some embodiments is configured to emit light into a sample vial region, measure light intensity of the light passing substantially through the sample vial region, detect a presence of a sample vial in the sample vial region using the measured light intensity, and determine one or more sample material characteristics of a sample material in the sample vial if the sample vial is present.

The measured light intensity in some embodiments comprises a light intensity of light received through the sample vial 10 with a dark value subtracted therefrom. The dark value comprises a light intensity measurement taken without light being emitted from the light source 6. The sample vial 10 may or may not be present in the apparatus 90 when the dark value is obtained.

The measured light intensity in some embodiments is resultant of a decrease in the intensity of light along the optical path due to absorption of light by the sample material. The measured light intensity in some embodiments is resultant of a decrease in the intensity of light along the optical path due to scattering of light by the sample material. The measured light intensity in some embodiments is resultant of a decrease in the intensity of light along the optical path due to scattering of light by the sample vial 10.

The measured light intensity in some embodiments is resultant of a decrease in the intensity of light along the optical path due to reflection of light propagating from a media of lower refractive index to a media of higher refractive index as result of a sample vial 10 of a higher refractive index being inserted into the optical path, with the optical path being of a lower refractive index. The measured light intensity in some embodiments is resultant of a decrease in the intensity of light along the optical path due to reflection of light propagating from a media of lower refractive index to a media of higher refractive index as result of a sample material of a higher refractive index being inserted into the optical path, with the optical path being of a lower refractive index.

The measured light intensity in some embodiments is resultant of a decrease in the intensity of light along the optical path due to absorption of light by a constituent of the sample material in proportion to the concentration of the constituent.

Light emitted from the light source 6 along the optical path impinges on the detector 4 (see FIG. 2), which generates a signal proportional to the intensity of the impinging light. But not all emitted light may reach the detector 4. The sample material may absorb some light, depending on the properties of the sample material. The automatic optical measurement apparatus 90 relies on the relationship of the absorption of light to the properties of the material through which the light propagates in order to determine characteristics of the sample material being tested.

The absorbance (A) is substantially equal to the product of molar absorptivity (e), the path length (L), and the concentration (c) of the solution to be measured, as given by:

$$A=(e)(L)(c) \tag{1}$$

This is known as the Beer-Lambert principle. The determined absorbance (A) relates the measured intensity of light without any sample material present (Io) (i.e., an empty measured intensity), to a measured sample material intensity (I'). The absorbance (A) can be determined according to:

$$A=-\log 10[(I')/(Io)] \tag{2}$$

The absorbance (A) can be determined by the automatic optical measurement apparatus 90. The absorbance (A) can be determined from the received/measured light intensity that is received after transit through the sample material. The absorbance (A) is therefore a determination of the amount of light absorbed by the sample material.

The absorbance (A) can be correlated to known absorption coefficients in order to determine one or more sample material characteristics. In some embodiments, the absorption coefficient of the sample material is substantially constant at a known wavelength of light. In some embodiments, the absorption coefficient of the sample material is substantially constant at a known bandwidth of light. In some embodiments, the absorption coefficient of the sample material is substantially constant at a known sample material thickness.

Loss in light intensity at the detector 4 occurs in the absence of sample material absorption due to reflection at the boundaries where the refractive index of the media through which the light propagates changes. The reflection loss (R), or Fresnel loss, for a single surface without absorption by the sample material can be calculated at a wavelength of light in accordance with the known equation:

$$R=[(n'-n)/(n'+n)]^2 \tag{3}$$

Where n=1.00 is the index of refraction of air, and n'=1.50 is the index of refraction of glass at a given wavelength of light. If the sample vial 10 is made of a different material than glass, then the vial index of refraction (n') could differ. The reflection loss factor (R) so calculated is equal to 0.04 for a single air-to-glass surface through which the light propagates.

When light passes completely through a sample material without absorption (other than air), a more complex relationship exists due to multiple internal reflections between the two air interfaces of the sample. In this scenario, the transmittance of light (T) is equal to:

$$T=(2n')/(1+n'^2) \quad (4)$$

This applies where the light originates in air and passes through a media with refractive index (n') normal to the optical surface and where the interference of light is negligible, as in the case of a thick-walled sample vial 10. For a glass vial of index of refraction n'=1.50 filled with a material of equal refractive index, such as a fill material that minimizes the reflection loss (R) by the sample/vial combination, the transmittance (T) is equal to 0.923 or a reflection loss factor of R=1-T, 0.077. This relates to the absorbance of A=−log 10 (0.923) or A=0.035 A. Therefore, if the threshold for the initiation of a measurement cycle is a value less than (Io) and greater than or equal to the minimum reflection loss case, then the measurement apparatus will be able to detect the presence of the sample vial 10 inserted along the optical path.

A measurement cycle is therefore initiated when the sample vial 10, (or other vessel, test tube, cuvette, et cetera), is inserted into the automatic optical measurement apparatus 90 so as to interrupt the optical path. The insertion will cause a decrease in the light impingent upon the detector 4, such that the received light will fall below a threshold signal value. A threshold signal value comprises a measurement value that is less than the signal generated by the detector 4 without a sample material present (less than 100% transmittance T). In addition, the threshold signal value must be greater than or equal to a signal value generated when the sample vial 10, including a medium of zero concentration functioning as a blank or zero absorption value, is inserted into the automatic optical measurement apparatus 90. The result of the insertion of the blank will be a signal value approximately equal to 100% $T(2n'/(1+n'^2)$, where n' is the refractive index of the sample vessel containing a sample of equal refractive index.

Determination of the concentration (c) of the sample 11 is result of the calculation:

$$c=A/(e)(L) \quad (5)$$

Where the absorption (A) of the sample material comprises A=−log 10(I'/Io), as previously discussed (see equation (2)). The (Io) term comprises (100% T transmittance−'dark' transmittance). The (I') term comprises ('measured' transmittance−'dark' transmittance). The (e) term comprises the molar absorptivity of the sample material at the measurement wavelength for a known sample thickness. The (L) term comprises L=(L')/(Lo) where the (Lo) term is the thickness of the laboratory sample (of the same material) at which the (e) term is determined and where the (L') term is the thickness of the sample material currently being measured.

An automatic optical measurement apparatus and method according to the invention can be used to determine concentration (c), molar absorptivity (e), sample thickness (L), and absorption (A) given the known values of the other terms of equation 5 and solving for the unknown term at a given wavelength of light. An automatic optical measurement apparatus and method according to one embodiment provides a measure of concentration. The apparatus and method according to another embodiment can provide automatic measure of concentration of a sample contained within a vessel upon insertion of the vessel into the apparatus without additional intervention by the operator. The apparatus and method according to another embodiment can provide automatic measure of concentration of a sample contained within a vessel upon insertion of the vessel into the apparatus without contamination or contaminate transfer to the apparatus. The apparatus and method according to all embodiments can provide automatic measure of concentration of a sample contained within a vessel upon insertion of the vessel into the apparatus wherein the measurement means is also used as the detector for presence or absence of the vessel or sample. The apparatus and method according to some embodiments can provide automatic measure of concentration of a sample contained within a vessel upon insertion of the vessel into the apparatus to provide repetitive capability of measurement upon removal of the vessel and insertion of a next vessel for which the concentration is to be determined without any additional intervention. The apparatus and method according to some embodiments can provide automatic measure of concentration of a sample contained within a vessel upon insertion of the vessel into the apparatus without contact to the apparatus. The apparatus and method according to some embodiments wherein hygiene of the internal workings is maintained and external surfaces are easily maintained. The apparatus and method according to some embodiments can provide an automatic measure of concentration of a sample contained within a vessel upon insertion of the vessel into the apparatus can maintain readiness for extended periods of time with minimal power consumption and minimal expenditure of lamp life. The apparatus and method according to some embodiments can provide automatic mathematically-derived results or statistical results of multiple measurements of a sample upon insertion of the sample into the apparatus.

Figure 2:
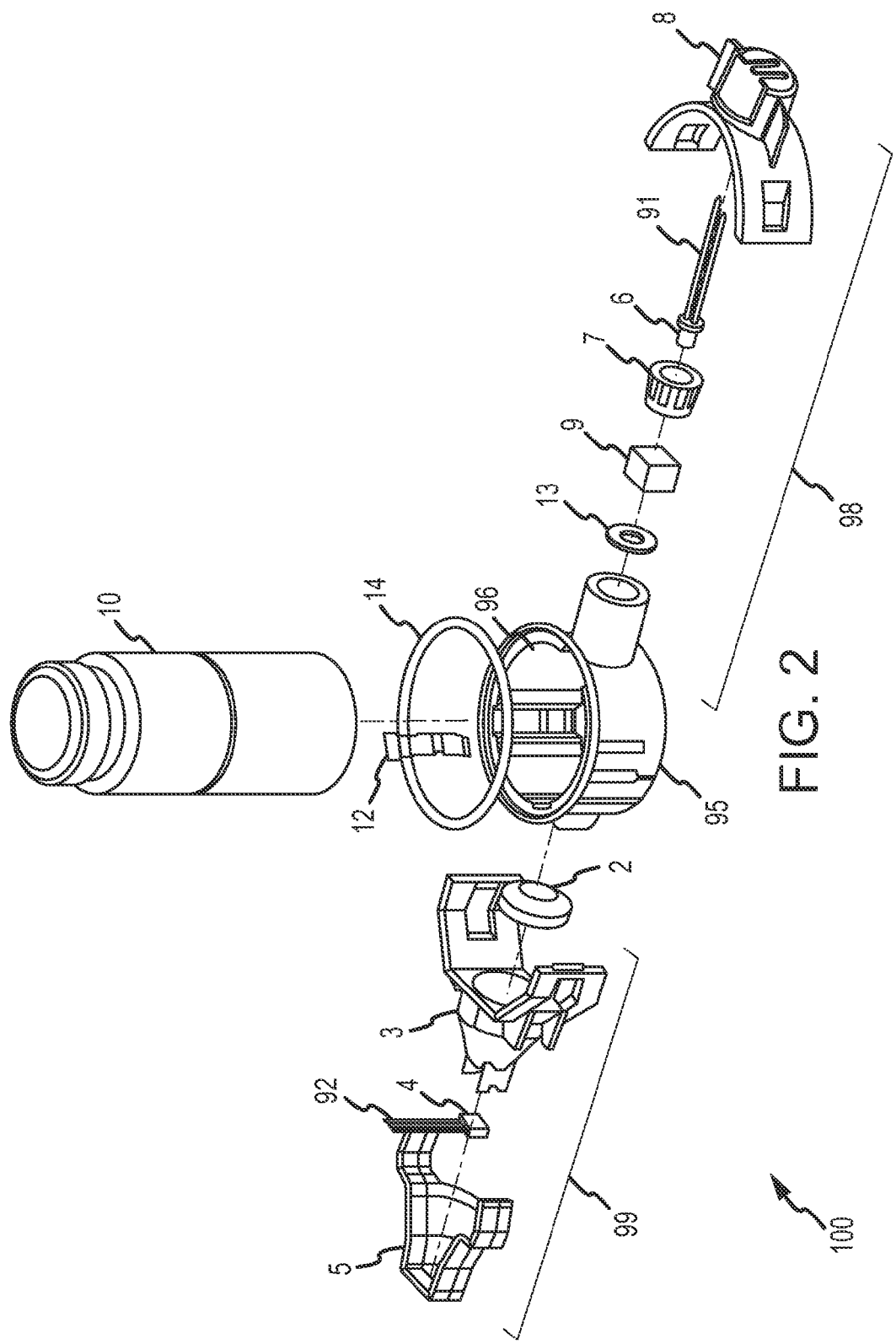
FIG. 2 shows detail of the automatic optical measurement system according to the invention.

FIG. 2 shows detail of the automatic optical measurement system 100 according to the invention. The automatic optical measurement apparatus 90 includes the body 95, the light source portion 98, and the light detector portion 99, as previously discussed.

The body 95 includes the measurement chamber 96 and can additionally include a seal member 14 and one or more biasing devices 12. The seal member 14 can substantially seal to the sample vial 10 when the sample vial 10 is inserted into the measurement chamber 96. The seal member 14 provides a barrier that prevents contamination of the measurement chamber 96 if sample material spillage occurs from (or near to) an upper portion of the sample vial 10. Conversely, if a lower portion of the sample vial 10 leaks the sample material, the contamination will be limited to the measurement chamber 96. The seal member 14 can comprise an O-ring, for example. However, other seal members can be employed.

In some embodiments, a seat 19 (see FIG. 9) can be provided on the outside surface of the sample vial 10. The seat 19 can correspond to and fit to the seal member 14 of the automatic optical measurement apparatus 90. Consequently, when the sample vial 10 is inserted into the measurement chamber 96, the seal member 14 can contact and seal to the seat 19, wherein the sample chamber 96 is substantially closed and sealed off during a measurement operation. Hygiene of the outside surface of the automatic optical measurement apparatus 90 and the inside volume of the measurement chamber 96 can thus be easily maintained by common methods of cleaning and disinfection, such as spraying, wiping, and other general cleaning methods. As a result, the automatic optical measurement apparatus 90 can be quickly and easily cleaned using soap or anti-bacterial agents, for example.

The one or more biasing devices 12 place a biasing force(s) on the sample vial 10 when the sample vial 10 is inserted into the measurement chamber 96. The one or more biasing devices 12 provide alignment of the sample vial with respect to the optical path by applying tension to the sample vial 10. The one or more biasing devices 12 in some embodiments operate to force the sample vial into a v-block feature in the measurement chamber 96. The v-block feature can comprise converging features that receive and guide a protrusion or protrusions on the sample vial 10. A v-block feature therefore can force an alignment during insertion and guide the insertion, can restrict movement during insertion and when seated, and can prevent movement after insertion. The biasing force(s) hold and stabilize the sample vial in the measurement chamber 96. In addition, the biasing force(s) resist insertion and removal, ensuring the stability of the sample vial 10. In an embodiment where the sample vial 10 is suspended within the measurement chamber 96 and within the optical path, no contact with the apparatus 90 is required in order to exercise an automatic measurement cycle. The one or more biasing devices 12 can comprise any manner of suitable devices, including springs or leaf springs, for example.

The light source portion 98 in some embodiments includes a light source 6 including the power leads 91, a light source bushing 7, a filter 9, an aperture 13, and a light source retainer 8. The light source retainer 8 can be fastened to the body 95 in any manner and holds the components of the light source portion 98 in position.

The light source 6 can comprise any suitable light source. The light source 6 is substantially co-linear with the detector 4. The light source 6 can emit visible and/or non-visible wavelengths of electromagnetic radiation to which detector 4 generates an electrical response. In some embodiments the light source 6 can comprise a light emitting diode (LED), infrared emitting diode (IrED), filament lamp, or discharge tube such as a fluorescent lamp or rare gas lamp. It should be understood that other light sources are contemplated and are within the scope of the description and claims.

The light source bushing 7 can hold the light source 6 in position and allows the positioning of the light source 6 to be adjusted. The light source bushing 7 provides a capability for positioning and aligning the light source 6, wherein the light source 6 can be positioned to be co-linear with the optical path. The light source bushing 7 includes an opening through which light is emitted by the light source 6. The light source bushing 7 and the aperture 13 are deployed along the optical path prior to the measurement chamber 96 so as to set a limit on the angular extent of rays emitted through the measurement chamber 96. This is accomplished by selecting openings wherein marginal rays emitted by the light source 6 will impinge upon the detector 4 regardless of presence or absence of the sample vial 10 and/or the sample material. The marginal ray restriction, to rays which will impinge upon the detector 4, is a detail of the invention that provides improved detection and measurability of the sample vial 10 and/or the sample material. However, it may be the case that light rays propagate into the measurement chamber 96 but do not impinge upon the detector 4 in the absence of the sample vial 10 and/or the sample material. Instead, the light rays may do so in the presence of the sample vial 10 and/or the sample material. This creates a condition in which more light is received in the detector 4 upon insertion, degrading the sample vial detection.

The filter 9 can be selected in order to pass a predetermined light frequency or band of light frequencies. The filter 9 is optionally employed along the optical path in order to eliminate some wavelengths and/or to reduce the bandwidth of light emission by the light source 6. Consequently, the filter 9 can comprise an absorption type filter or interference filter, as examples. This may be done when a bandwidth smaller than that of the light source's natural emission is desired. The reduction in the bandwidth, though not required, can be useful for gaining an increase in sensitivity of the measurement by restricting the emission wavelength to predetermined light wavelengths where absorption by the sample material is greatest, or for improving the linearity of response of absorption as result of concentration or thickness changes of the sample material. This is also sometimes desirable in order to increase the sensitivity of the apparatus for the measure of a concentration, thickness, or molar absorptivity of a particular sample by restricting the wavelength of transmittance to a wavelength of light that is highly dependent on these properties of the sample. Consequently, the use of and selection of the filter 9 may depend on the nature of the sample material to be tested and the desired constituent of the sample to be measured.

The aperture 13 may be used to pass a light beam of a predetermined extent. As a result, light emitted into the measurement chamber 96 comprises a tightly focused beam that is substantially centered about the optical path.

It should be understood that the components of the light source portion 98 can be varied as needed. For example, the filter 9 and the aperture 13 can be omitted or can include multiple elements or components instead of single elements. In addition, other optical elements are contemplated and are within the scope of the description and claims.

The light detector portion 99 in some embodiments includes a lens 2, a lens retainer 3, a detector 4 including the measurement leads 92, and a detector retainer 5. The detector retainer 5 and the lens retainer 3 can be fastened to the body 95 in any manner. These two retainers hold and align lens 2 and the detector 4 in position along the optical axis.

Lens 2 can comprise any suitable lens. Lens 2 focuses the light passing through the measurement chamber 96. Lens 2 is substantially aligned with the optical axis and with the aperture 13 of the light source portion 98. Lens 2 in some embodiments restricts the field of view of the detector 4 to the field of light emitted by the light source 6 through the aperture 13. Lens 2 can be provided in order to focus and direct the emitted light from source portion 98 onto the detector 4.

Where the detector 4 is small in size or limited in detection area, the lens 2 may be deployed along the optical path prior to the detector 4. The focal length and spatial relationship to the detector 4 and the aperture 13 are selected so as to provide an optimum field of view for the detector 4. The field of view therefore can include marginal rays emitted through the aperture 13 regardless of the presence or absence of the sample vial 10 or the sample material. Optionally, or in addition to lens 2, other and additional lenses may be formed or located integral to the measurement chamber 96 as one or more transparent surfaces for the transmittance of light through the measurement chamber 96. This may be done to further define the ray paths through the measurement chamber 96 or to improve the field of view of the detector 4. It may also be done in order to reduce or compensate for optical aberrations caused by differences in the ray paths through the measurement chamber 96, such as those caused by the curvature of the sample vial 10 and the presence of the sample material.

The detector 4 receives the light and generates an electrical measurement signal related to the light impingent upon the light sensitive surface of the detector. In some embodiments, the electrical measurement signal is proportional to or otherwise related to a received light intensity. Alternatively, or in addition, the electrical measurement signal can be related to a received light frequency and/or received light bandwidth.

The light source 6 and the detector 4 are separated so as to allow for the placement of the sample vial 10 and the sample material therebetween. The sample vial 10 can be inserted between the light source 6 and the detector 4 for a measurement.

It should be understood that the components of the light detector portion 99 can be varied as needed. For example, lens 2 can be omitted or can include multiple elements or components instead of single elements. In addition, other optical elements are contemplated and are within the scope of the description and claims.

Figure 3:
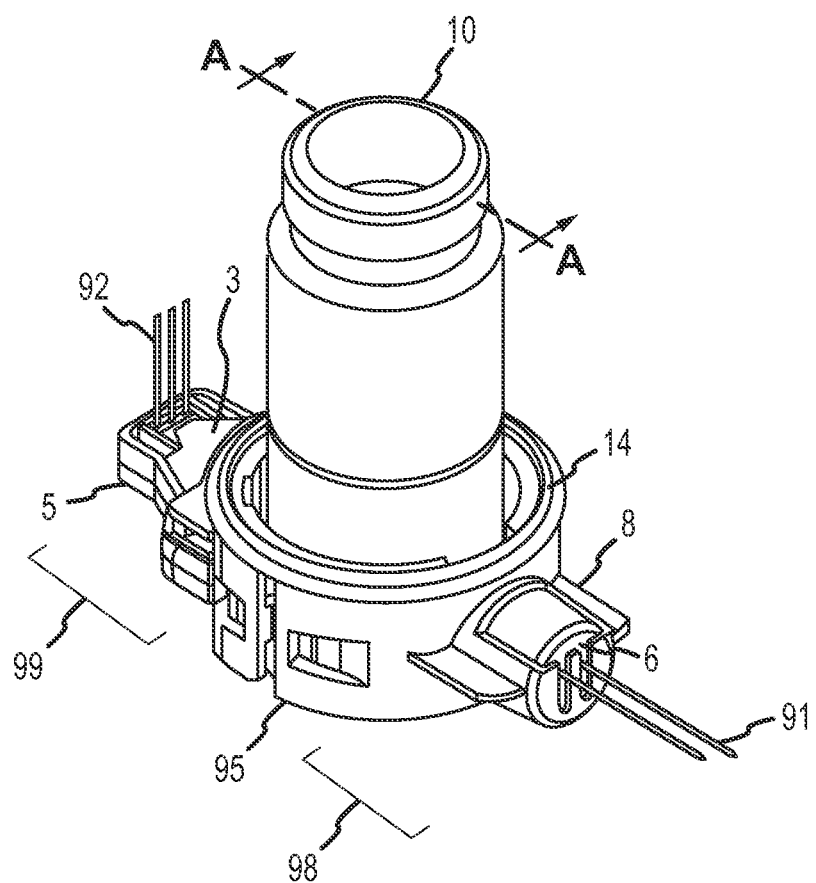
FIG. 3 shows a sample vial in position in the automatic optical measurement system.

FIG. 3 shows the sample vial in position in the automatic optical measurement system 90. It can be seen from the figure that the sample vial 10 is seated at least partially in the measurement chamber 96. Light emitted by the light source portion 98 passes through the sample vial 10 in order to reach the light detector portion 99. Consequently, the optical path through the measurement chamber 96 is interrupted by the sample vial 10 and properties of the light will be affected by any sample material in the sample vial 10.

Figure 4:
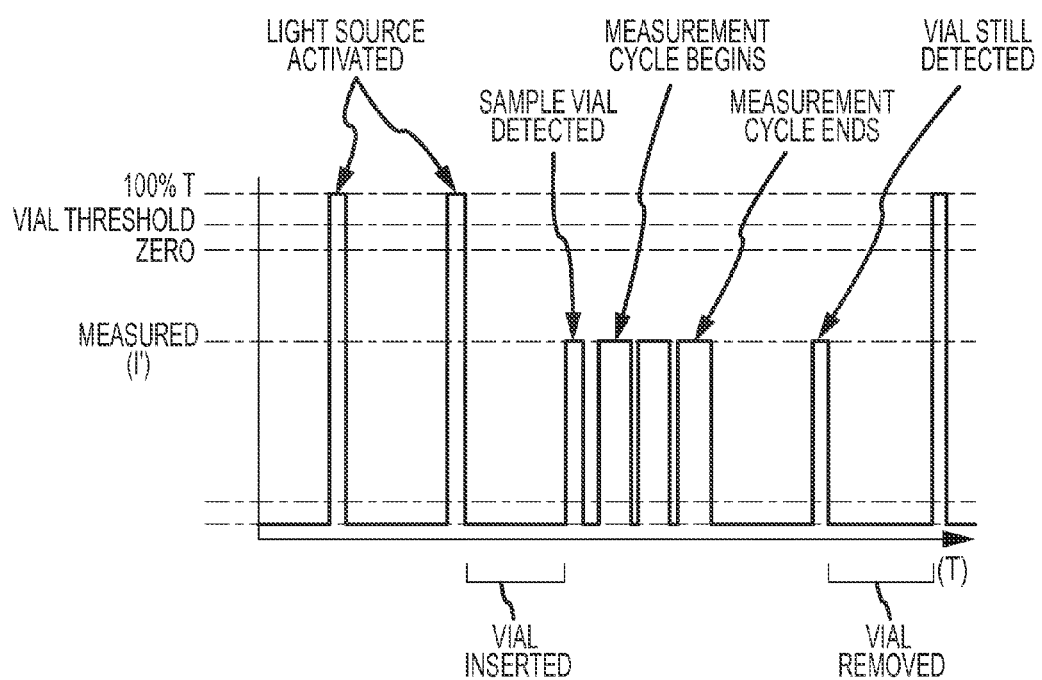
FIG. 4 is a diagram of a typical light intensity measurement sequence at a detector over time.

FIG. 4 is a diagram of a typical light intensity measurement sequence at the detector 4 over time. The diagram further illustrates the operation of the invention. The diagram shows that the light intensity can vary from 0% T (total absorption of light) to 100% T (total transmission of light) when the light source 6 is activated. The measured light may be between the dark value and the 0% T value when the light source 6 is off.

If the light intensity value produced by the detector 4 does not reach or exceed the 0% T threshold, then it can be determined that the light source 6 has not been activated. Any light measurement generated by the detector 4 that is below the 0% T level is the result of detected ambient light or an error signal (such as that due to detector leakage current), and the dark signal is not result of the detection of light emitted from the light source 6.

It can be seen that the light source 6 is switched off during 'dark' measurements, as previously described. Consequently, the light source 6 may be energized only periodically or intermittently. The emission by the light source 6 is not required during wait times and is useful in conservation of electrical power and/or lamp life. The control of light propagation can be by control of electrical power to the light source 6 or by mechanical gating of light propagation by an opaque media inserted along the optical path subsequent to light source 6, such as a shutter, filter, etc.

The 'dark' signal may be the result of ambient light being received by the detector 4. The 'dark' signal may also be the result of detector leakage current. The 0% T signal value is generally greater than the 'dark' signal value due to stray light emitted by light source 6, which does not propagate through the sample 11 or vessel 10 and includes the 'dark' signal value as well. The signal value at 0% T represents a measurement where a high absorption of light occurs, including the condition where total light absorption by the sample occurs. The first two signal events in the diagram comprise light intensity measurements taken with no sample vial 10 present. The light source 6 is energized during the first two signal events, creating the first two signal events, even though the sample vial 10 is not present. As a result, the light intensity measurements result in a substantially one hundred percent light transmittance, at the 100% T value.

In between activations of the light source 6 are low-level dark measurements, i.e., light intensity measurements that can be taken when the light source 6 is not energized. The dark measurements can be used to quantify the amount of ambient light being received by the detector 4. Consequently, a dark signal value can be subtracted from other measurements as a correction, removing ambient light from any measurement values.

The vial threshold, shown less than the 100% T maximum transmittance value and greater than the 'zero' absorption value, comprises a predetermined vial detection transmittance value. Consequently, when the measured light intensity is below or equal to the vial threshold, then the sample vial 10 is reducing the light intensity emitted by light source 98 and is subsequently detected.

A sequence of detectable events occurs to initiates a measurement cycle when a previous measured light intensity is greater than the vial threshold and the current light intensity measurement is less than the vial threshold, resulting in the detection of the presence of sample vial 10 and subsequent initiation of a measurement cycle by the processor 93. A measurement cycle may be a single reading or several readings taken in succession for mathematical enhancement of the resultant value. Multiple readings may provide better precision by noise reduction via calculation of an average signal value. Multiple readings may provide a minimum and/or maximum signal value over the duration the measurement cycle or some other statistical measure of the sample or vessel.

The third signal event comprises a sample vial detected value. The third signal event comprises a measurement cycle initiated at or after a sample vial insertion. The fourth, fifth, and sixth signal events comprise measurement cycles that measure an interaction of the light with any sample material in the sample vial 10 or sample within measurement chamber 96. Multiple measurement cycles may occur. The number of measurement cycles may depend on a light source activation period and on the duration of the inserted time of the sample vial 10 in the measurement chamber 96.

After a successful measurement cycle, the activation periods of the light source 6 may be spaced farther apart in order to conserve power, as is shown at the seventh signal event. At the seventh signal event, a vial-still-detected condition exists and assay of the sample is not required at this point in time and may or may not be obtained.

At the eighth signal event, the light intensity measurement returns to approximately the 100% T transmittance value. This indicates that the sample vial 10 has been removed.

The figure shows one or more sample vial detection cycles followed by one or more light intensity measurement cycles. The figure therefore shows distinct detection and measurement cycles. However, it should be understood that the detection function and the measurement function could be combined into one light emission and quantification step. A sample vial detection cycle produces a light intensity measurement, and this light intensity measurement could be immediately used for determining sample material characteristics or could be one of multiple light intensity measurement values.

Figure 5:
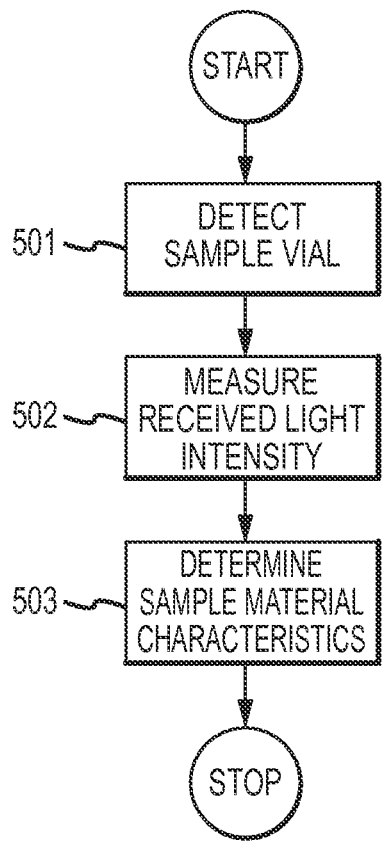
FIG. 5 is a flowchart of an automatic optical measurement method according to the invention.

FIG. 5 is a flowchart 500 of an automatic optical measurement method according to the invention. In step 501, a sample vial is detected in a measurement chamber. The sample vial is detected according to the effect of the sample vial on received light, as previously discussed. The presence of the sample vial will decrease the intensity of received light, wherein the received light is detected and measured after the measurement chamber.

In step 502, the intensity of received light is measured. The measurement may comprise a measurement performed on the light received in step 501 above. Alternatively, the measurement may be subsequent to the sample vial detection step, wherein both steps receive and measure light that has passed through the measurement chamber. As a consequence, the light has been affected by the sample vial, if present in the measurement chamber, as discussed above. As a consequence, the light has been affected by the sample material, if present in the sample vial. In step 503, one or more sample material characteristics are determined from the measured light intensity, as previously discussed.

Figure 6:
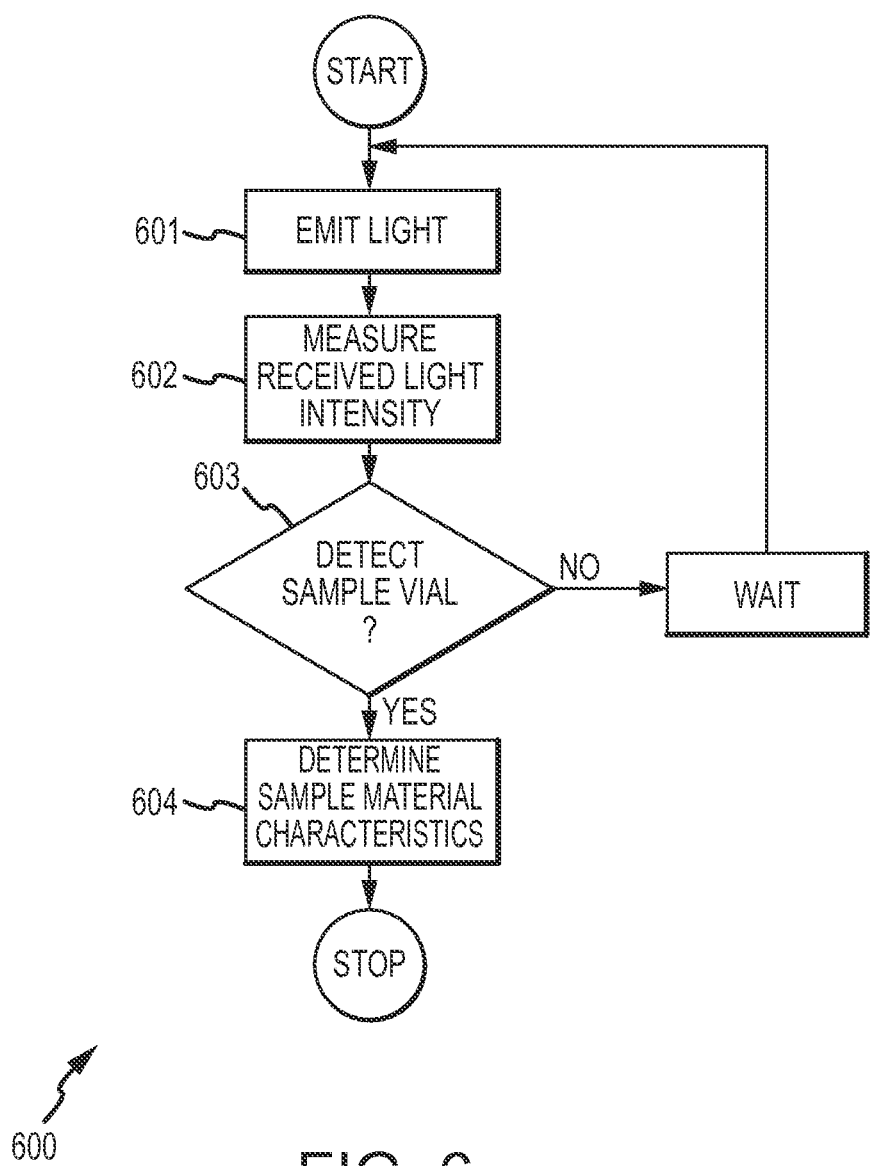
FIG. 6 is a flowchart of an automatic optical measurement method according to the invention.

FIG. 6 is a flowchart 600 of an automatic optical measurement method according to the invention. In step 601, light is emitted through a measurement chamber. The light emission can be substantially constant or can be intermittent or periodic. The measurement chamber may or may not include a sample vial. The sample vial may or may not include a sample material within. The light will be affected by the presence of the sample vial in the measurement chamber. The light will be affected by the presence of the sample material in the sample vial.

In step 602, the intensity of received light is measured. The received light has passed through the measurement chamber. As a consequence, the light has been affected by the sample vial, if present in the measurement chamber. As a consequence, the light has been affected by the sample material, if present in the sample vial.

In step 603, the measured light intensity is used to determine the presence or absence of the sample vial, as previously discussed. If the sample vial is detected, then the method proceeds to step 604. If the sample vial is not detected, then the method branches back to step 601. A wait period may be included, wherein the branching occurs after a predetermined time. After the branching, the light emission, measurement, and detection are repetitively performed.

In step 604, one or more sample material characteristics are determined from the measured light intensity, as previously discussed.

Figure 7:
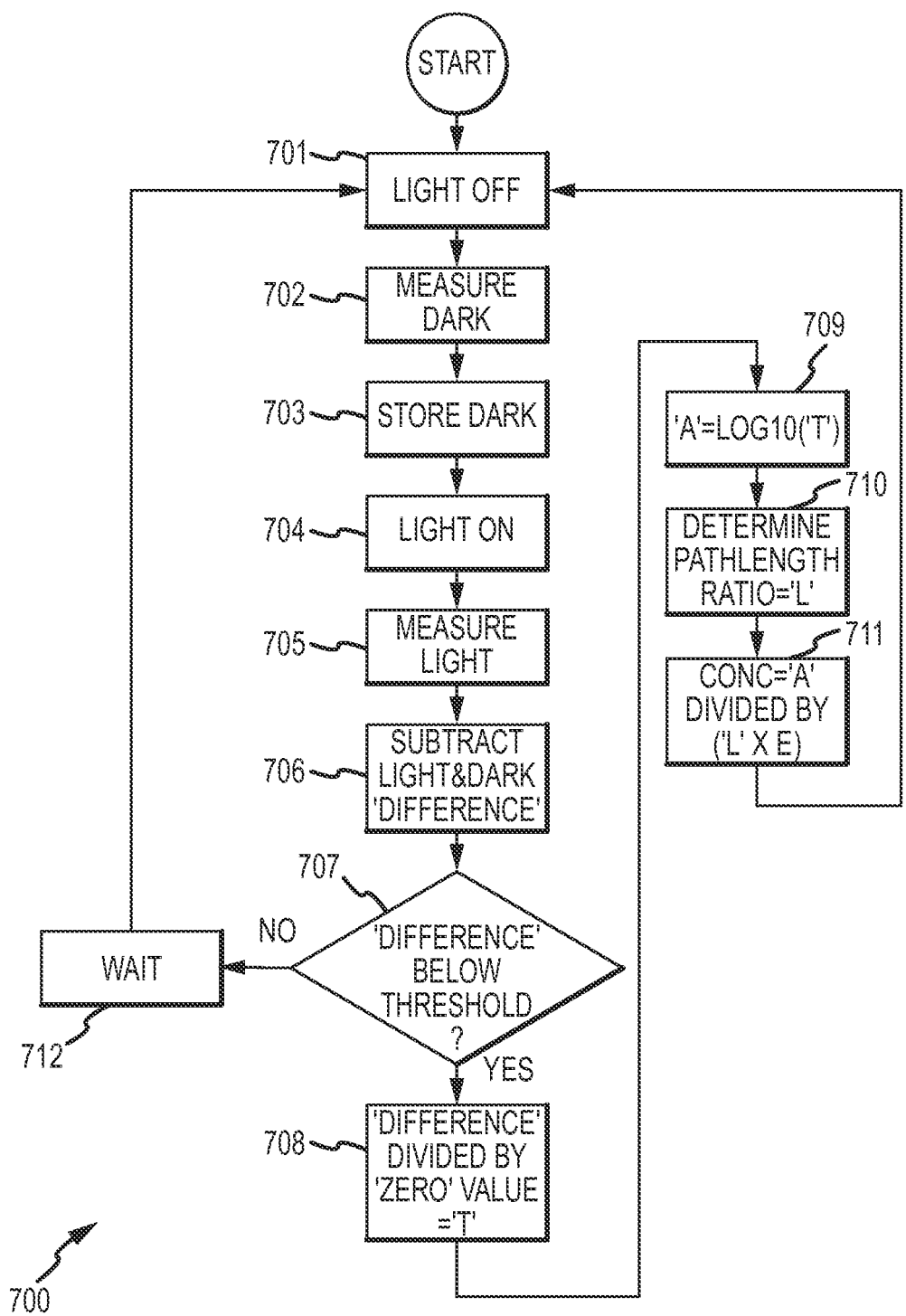
FIG. 7 is a flowchart of a method for the detection of presence of a sample vial and for the measure of the sample vial contents.

FIG. 7 is a flowchart 700 of a method for the detection of presence of a sample vial and for the measure of the sample vial contents, specifically concentration, for example. In step 701, light is not permitted to propagate along an optical path.

In step 702, measure a dark signal comprising a light intensity measurement without a light source being energized.

In step 703, store the signal value generated by the detector as a 'dark' signal value.

In step 704, a light source is turned on.

In step 705, measure the intensity of the light impingent upon the detector as a 'measured' signal value.

In step 706, determine the difference in signal value between the 'measured' signal value and the 'dark' signal value as a 'difference' value.

In step 707, determine that the 'difference' value is less than or equal to the stored 'vial threshold' value. The 'vial threshold' value comprises a value greater than a signal value generated by the detector with no sample vial present along the optical path. A zero absorption value, by comparison, comprises a light intensity measurement for a sample vial and reference sample material of zero concentration and of known thickness as a 'zero' signal value.

In step 708, if the 'measured' signal value is less than or equal to the stored 'threshold' value and the 'previous' measured signal value was greater than the stored 'threshold' value, then determine a 'transmittance ratio' value of the 'difference' value divided by the stored 'zero' value.

In step 709, if the 'measured' signal value is less than or equal to the stored 'threshold' value and the 'previous' measured signal value was greater than the stored 'threshold' value, then determine the 'absorbance' value of the sample as the −log 10 of the 'transmittance ratio' value.

In step 710, if the 'measured' signal value is less than or equal to the stored 'threshold' value and the 'previous' measured signal value was greater than the stored 'threshold' value, then determine the 'path length ratio' as the 'sample thickness' divided by the 'reference thickness' related to the sample thickness at which the 'absorption coefficient' is known.

In step 711, if the 'measured' signal value is less than or equal to the stored 'threshold' value and the 'previous' measured signal value was greater than the stored 'threshold' value, then determine a 'concentration' value as the 'absorbance' value divided by the product of the 'path length ratio' and the 'molar absorptivity' for the sample.

In step 712, a wait period is enforced. The wait period can be optional or mandatory. The wait period occurs if the difference in signal value in step 707 is less than or equal to the stored 'vial threshold' value. The wait can comprise a predetermined wait period.

Figure 8:
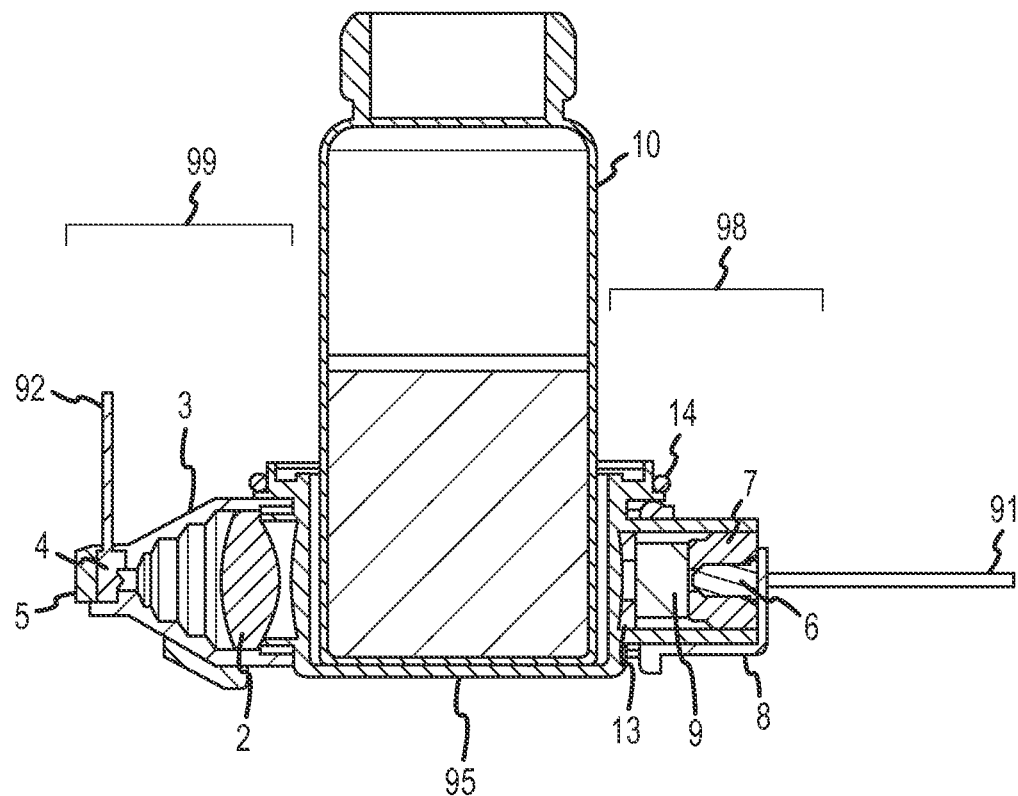
FIG. 8 is a section view AA of the automatic optical measurement system according to the invention.

FIG. 8 is a section view AA of the automatic optical measurement system 100 according to the invention. The section view AA again shows the components of the light source portion 98 and the light detector portion 99 and their respective arrangements. It is clear from the figure that the sample vial 10 interrupts the optical path from the light source 6 to the detector 4.

Figure 9:
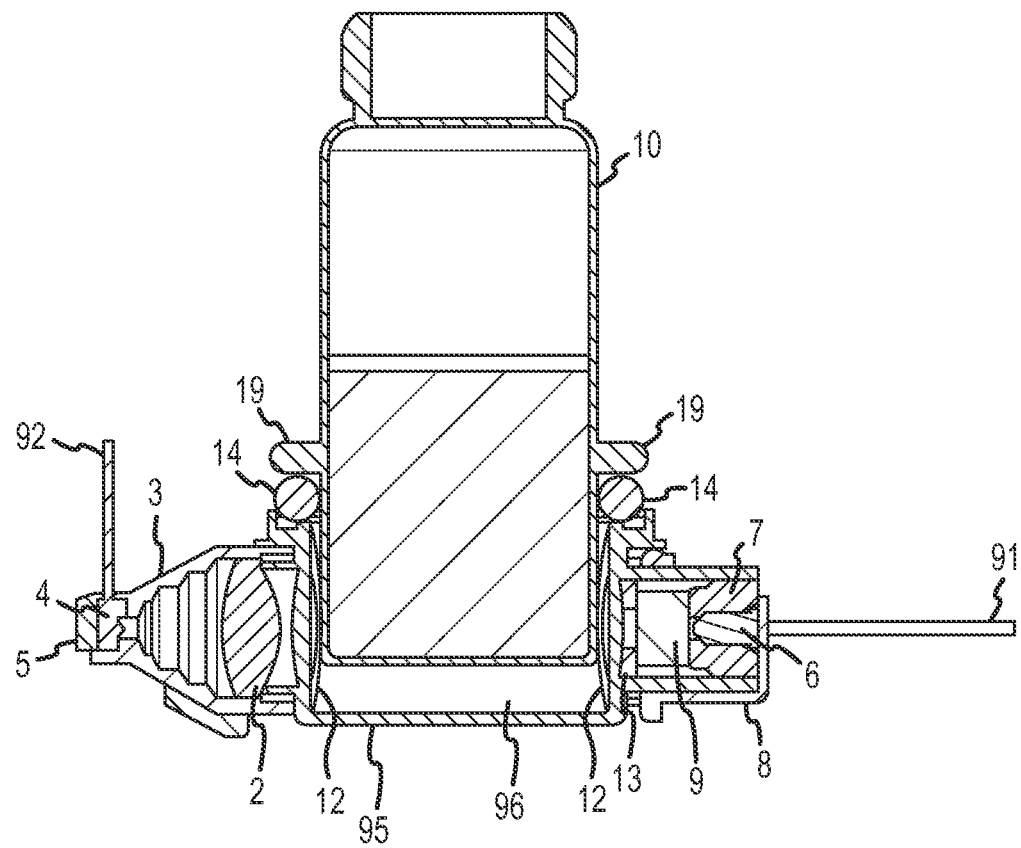
FIG. 9 is a section view AA of the automatic optical measurement system according to the invention.
Figure 9:

FIG. 9 is a section view AA of the automatic optical measurement system 100 according to the invention. This version of the section view AA additionally shows the biasing devices 12 interacting with the sample vial 10. In this figure, the biasing devices 12 contact the sample vial 10 and hold the sample vial 10 from bottoming out in the measurement chamber 96. Alternatively, the sample vial 10 can rest on the bottom of the measurement chamber 96.

In some embodiments, the sample vial 10 can include a seat 19 that contacts the seal member 14 to create a seal. In addition, the seat 19 prevents the sample vial 10 from bottoming out in the measurement chamber 96 and supports the sample vial 10 in a stable fashion. However, the sample vial 10 still interrupts the optical path from the light source 6 to the detector 4. The seal created by the seat 19 and the seal member 14 ensures that any leakage into the measurement chamber 96 is contained. In addition, any leakage or spillage of any material above the seat 19 cannot enter the measurement chamber 96.

In accordance with the invention, an automatic optical measurement apparatus and method is presented which includes an optical path along which light from a light source propagates to impinge upon a detector. A measurement cycle is initiated when the signal value of the detector decreases to a value less or equal to the stored 'threshold' value from a previous value greater than the 'threshold' value; a 'threshold' value of value greater than signal value generated by the detector with present along the optical path, a vessel and reference sample of zero concentration and of known thickness as a 'zero' signal value, and less than the signal value generated by the detector with no vessel present along the optical path. Thus, an automatic measurement cycle is initiated upon insertion of a vial or vessel along the optical path of the apparatus, and re-initiated with subsequent removal and insertions of the vial or vessel without manual manipulation of the controls of the apparatus nor any additional means for the detection of presence of the sample vessel in order to initiate the measurement cycle.

An automatic measurement initiated by the detection of the vessel along the optical path requires only a single measurement value be stored within the apparatus; that of a reference sample of zero concentration and of known thickness as a 'zero' signal value minus the 'dark' signal value. The 'zero' value is a constant for a given sample liquid and vessel material of known refractive index and can be calculated for a given wavelength and permanently stored within the apparatus for future reference. When the sample is undetermined prior to use, a measure of the 'zero' can be made and stored for reference by the apparatus. No other conditions need exist prior to the execution of the automatic measurement method, though knowledge of the 0% T signal value, as a stored measure of a high absorption sample 11 is useful for improvement of the determination of concentrations where the absorption by the sample is high.

Light need not be emitted constantly for the detection of the vessel, nor during the wait time. In the preferred embodiment of the invention, the light source is configured to emit intermittently in order to extend the battery life, extend the life of the light source, or both. In some embodiments, the user can turn electrical power on and off, such as at the beginning and end of a measurement process or sequence of measurements, such as through an external or internal switch or contact, for example. A further extension of the battery life and lamp life may be realized in the present invention by employing a reduced measurement cycle or single measurement event for the detection of the presence of the vessel within the optical path which is short in duration and low in precision; precision adequate for the determination of vial presence, but not as precise as to determine value of the unknown sample parameter to the required fraction. The duration of the wait time with the lamp off is judiciously selected so as to be short enough in duration as to not miss the shortest elapsed time interval of removal and subsequent insertion of the vessel along the optical path.

What is claimed is:

1. An optical measurement method, comprising:
   emitting light into a sample vial region using a light source;
   detecting with a detector light intensity of the light passing substantially through the sample vial region;
   measuring the intensity of light detected;
   detecting a presence of a sample vial in the sample vial region without contact to the sample vial region based on the measured light intensity transitioning a threshold; and
   responsive to detecting the presence of a sample vial in the sample vial region, determining one or more sample material characteristics of a sample material in the sample vial based on the measured light intensity.

2. An optical measurement apparatus comprising:
   a light source configured to emit light into a sample vial region;
   a detector configured to detect light intensity of the light passing substantially through the sample vial region, the detector further configured to generate a signal proportional to the intensity of light detected; and
   at least one processor configured to:
   use the signal to detect the presence of the sample vial in the sample vial region without contact to the sample vial region responsive to the signal transitioning a threshold; and
   responsive to detecting the presence of a sample vial, determine one or more sample material characteristics of a sample material in the sample vial using the signal.

3. The optical measurement system of claim 2, wherein the at least one processor operates the light source to emit light into the sample vial region subsequent to detecting the presence of the sample vial in the sample vial region.

4. The optical measurement system of claim 3, wherein the at least one processor uses a signal generated after detecting the presence of the sample vial in the sample region to determine one or more sample material characteristics of the sample material in the sample vial.

5. The optical measurement instrument of claim 2, wherein the at least one processor is further configured to:
   determine that a sample vial is not present in the sample vial region using the signal;
   cause the light source to cease emitting light into the sample vial region in response to determining that a sample vial is not present in the sample vial region.

6. The optical measurement instrument of claim 5, wherein the at least one processor is further configured to wait a predetermined time prior to operating the light source to emit light into the sample vial region responsive to determining that a sample vial is not present in the sample vial region.

* * * * *